US012576091B2

(12) United States Patent
Zhan et al.

(10) Patent No.: US 12,576,091 B2
(45) Date of Patent: Mar. 17, 2026

(54) PREPARATION METHOD OF SALFAPRODIL FREEZE-DRIED POWDER INJECTION, AND PRODUCT AND USE THEREOF

(71) Applicant: GNT PHARMA CO., LTD., Yongin-si (KR)

(72) Inventors: Weiqiang Zhan, Zhejiang (CN); Zhanguo Wang, Zhejiang (CN); Wei Zhang, Zhejiang (CN); Lingyan Fu, Zhejiang (CN); Qian Lin, Zhejiang (CN); Xiaoli Chen, Zhejiang (CN); Guoyang Lv, Zhejiang (CN); Liyin Zhong, Zhejiang (CN); Xinliang Xu, Zhejiang (CN); Fangmeng Zhu, Zhejiang (CN)

(73) Assignee: GNT PHARMA CO., LTD., Gyeonggi-do (KR)

( * ) Notice: Subject to any disclaimer, the term of this patent is extended or adjusted under 35 U.S.C. 154(b) by 519 days.

(21) Appl. No.: 18/007,020

(22) PCT Filed: Jul. 27, 2021

(86) PCT No.: PCT/CN2021/108541

§ 371 (c)(1),
(2) Date: Jan. 26, 2023

(87) PCT Pub. No.: WO2022/022483

PCT Pub. Date: Feb. 3, 2022

(65) Prior Publication Data

US 2023/0270757 A1 Aug. 31, 2023

(30) Foreign Application Priority Data

Jul. 27, 2020 (CN) ......................... 202010729677.4

(51) Int. Cl.

| | |
|---|---|
| ***A61K 31/606*** | (2006.01) |
| ***A61K 9/00*** | (2006.01) |
| ***A61K 9/19*** | (2006.01) |

(52) U.S. Cl.

CPC .......... *A61K 31/606* (2013.01); *A61K 9/0019* (2013.01); *A61K 9/19* (2013.01)

(58) Field of Classification Search

CPC ................................ A61K 9/19; A61K 9/0019
USPC .......................................................... 514/166
See application file for complete search history.

(56) References Cited

U.S. PATENT DOCUMENTS 9,308,174 B2 * 4/2016 Turchetta et al. ....... A61K 9/19 514/394

FOREIGN PATENT DOCUMENTS

| | | | | |
|---|---|---|---|---|
| CN | 1309703 C | | 4/2007 | |
| CN | 101180263 A | | 5/2008 | |
| CN | 102617383 A | | 8/2012 | |
| CN | 104771369 A | | 7/2015 | |
| CN | 104817465 A | | 8/2015 | |
| CN | 106831462 A | | 6/2017 | |
| EP | 3323410 A1 | * | 5/2018 | ................ A61P 7/00 |
| WO | WO 2004/000786 A1 | | 12/2003 | |
| WO | WO2006126846 A1 | * | 11/2006 | ........... C07C 213/02 |
| WO | WO2013139143 A1 | * | 9/2013 | ........... C07C 229/64 |
| WO | WO 2021/181159 A1 | | 9/2021 | |

OTHER PUBLICATIONS

Extended European Search Report issued in European Patent Application No. 21848554.8, dated Aug. 12, 2024 in 19 pages.

International Search Report mailed Nov. 1, 2021 in International Application No. PCT/CN2021/108541.

* cited by examiner

*Primary Examiner* — Jeffrey S Lundgren
*Assistant Examiner* — Heather Dahlin
(74) *Attorney, Agent, or Firm* — Harness, Dickey & Pierce, P.L.C.

(57) ABSTRACT

A salfaprodil freeze-dried powder injection, and a preparation method thereof and the use thereof are proposed. The preparation method may include adding salfaprodil into water for injection, filtering after the salfaprodil is completely dissolved, and adjusting pH of filtrate with an alkaline substance water solution. The method may also include adding the injection water to achieve a constant volume, filling with an inert gas for protection, and performing sterilization and filtration to obtain a salfaprodil solution, which is then freeze-dried to obtain the salfaprodil freeze-dried powder injection.

8 Claims, No Drawings

PREPARATION METHOD OF SALFAPRODIL FREEZE-DRIED POWDER INJECTION, AND PRODUCT AND USE THEREOF

REFERENCES TO RELATED APPLICATIONS

The present application is a U.S. national phase application under 35 U.S.C. § 371 of International Application No. PCT/CN2021/108541, filed on Jul. 27, 2021, which claims the benefit of Chinese Patent Application No. 202010729677.4 filed on Jul. 27, 2020, the entire disclosure of each of which is incorporated herein by reference.

TECHNICAL FIELD

The present invention belongs to the technical field of pharmaceutical formulation and relates to a preparation method of salfaprodil freeze-dried powder injection, and product and medical use thereof.

BACKGROUND ART

The chemical name of salfaprodil is potassium 2-hydroxy-5-[2,3,5,6-tetrafluoro-4-(trifluoromethyl)benzylamino]benzoate, and its structural formula is as follows:

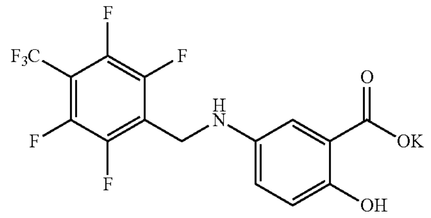

Salfaprodil acts as a N-methyl-D-aspartate (NMDA) receptor antagonist of moderate intensity and acts as a potent antioxidant giving a dual neuroprotective effect and is capable of simultaneously blocking NMDA receptor-mediated excitotoxicity and the body's oxidative stress response. The neuroprotective effect can last for 28 days or longer, leading to the expansion of the therapeutic time window along with an extensive neuroprotective action.

CN1309703C discloses that salfaprodil can be used for the treatment of conventional or pathological neurological disorders in cerebrovascular and neurological diseases and symptoms. Particularly, salfaprodil can be used to prevent and treat thromboembolism, ischemic stroke, hemorrhagic stroke, cerebral vasospasm, brain aging, traumatic brain injury, traumatic spinal cord injury, cardiac arrest, arterial hypotension, hypoglycemia, hypoxia, and tissue hypoxia. In addition, salfaprodil may be effective in treating neurodegenerative diseases such as Huntington's Disease (HD), Alzheimer's Disease (AD), olivopontocerebellar degeneration, amyotrophic lateral sclerosis (ALS), Parkinson's Disease (PD), Down's Syndrome (DS), epilepsy, multi-infarct dementia, and encephalitis.

Conventional freeze-dried formulations have a variety of preparation methods and are extensively used for various types of powder injection. However, when preparing salfaprodil for injection by the process used by other varieties in the prior art (e.g., fludarabine phosphate freeze-drying method of CN104771369B), it is difficult to form a uniform and fine crystal during freeze-drying due to the difference in crystallization between active ingredients with different therapeutic efficacy. Additionally, precipitation occurs in the product after reconstitution, resulting in poor stability, apparent layering, and other defects. Therefore, it is urgently needed to develop a freeze-dried formulation preparation method suitable for salfaprodil for injection.

CONTENTS OF THE INVENTION

Problem to be Solved

In order to overcome the shortcomings of using the existing freeze-drying techniques to prepare salfaprodil for injection, this invention provides a preparation method of salfaprodil for injection and products prepared by this method which have superior formability, visually clear pre-freeze-drying solution, good re-solubility of the freeze-dried products, good transparency after reconstitution, low impurity content, high stability, and controllable quality.

Means to Solve the Problem

The present invention has been realized in the following ways:

First, the present invention provides a preparation method of salfaprodil freeze-dried powder injection, comprising the following procedures: adding and dissolving salfaprodil into water for injection; filtering the solution; adjusting pH filtrate with alkaline substance water solution; adding water for injection to achieve constant volume and filling it with inert gas for protection, performing sterile filtration to obtain salfaprodil solution, then freeze-drying the solution to obtain salfaprodil freeze-dried powder injection.

Preferably, the pore size of each of the filter membranes used for filtration and sterile filtration in the preparation method is 0.2 to 1.0 μm.

More preferably, the material of the filter membrane used for filtration and sterile filtration in the preparation method is polyethersulfone (PES), polytetrafluoroethylene (PTFE), nylon (N6/N66), or polyvinylidene fluoride (PVDF).

Preferably, the alkaline substance used in the preparation method is selected from potassium hydroxide, potassium carbonate, potassium bicarbonate, sodium hydroxide, sodium carbonate, and sodium bicarbonate.

Preferably, the alkaline substance water solution used in the preparation method has a concentration of 0.1 to 1.0M.

Preferably, the pH in the preparation method is adjusted to between 8.0 to 10.0.

Preferably, the inert gas used in the preparation method is argon or nitrogen.

Preferably, sterile filtration in the preparation method is performed within 16 hours after achieving constant volume.

Preferably, the weight per volume concentration of salfaprodil solution in the preparation method is 5 to 20 w/v %.

Preferably, freeze-drying in the preparation method is performed in a freeze dryer and involves a pre-freezing, temperature recovery, re-cooling, primary drying a, primary drying b, and desorption drying stages.

More preferably, the plate layer temperature of the freeze dryer is lowered to between −50 to −30° C. and kept at a constant temperature for 1 to 3 hours during the pre-freezing stage.

More preferably, the plate layer temperature of the freeze dryer is raised to between −5 to 5° C. and kept at a constant temperature for 1 to 3 hours during the temperature recovery stage.

More preferably, the plate layer temperature of the freeze dryer is lowered to between −50 to −30° C. and kept at a constant temperature for 1 to 3 hours during the re-cooling stage.

More preferably, the plate layer temperature of the freeze dryer is raised to between −30 to −25° C. and kept at a constant temperature for 10 to 30 hours during the primary drying a stage. The vacuum degree is 5 to 20 Pa.

More preferably, the plate layer temperature of the freeze dryer is raised to between 5 to 20° C. and kept at a constant temperature for 10 to 30 hours during the primary drying b stage. The vacuum degree is 5 to 20 Pa.

More preferably, the plate layer temperature of the freeze dryer is raised to between 10 to 40° C. and kept at a constant temperature for 10 to 30 hours during the desorption drying stage. The vacuum degree is 5 to 20 Pa.

Preferably, the preparation method includes filling, caulking, capping, and/or packaging.

Second, the present invention provides a salfaprodil freeze-dried powder injection that is prepared using the preparation method.

Preferably, salfaprodil in the salfaprodil freeze-dried powder injection is the only active pharmaceutical ingredient.

Third, the present invention provides the use of the salfaprodil freeze-dried powder injection in preparing medicines for the prevention and/or treatment of neurodegenerative diseases.

Preferably, the neurodegenerative diseases are selected from one or more of Huntington's Disease (HD), Alzheimer's Disease (AD), Pick's Disease (PD), Korsakov's Syndrome (KS), olivopontocerebellar degeneration, amyotrophic lateral sclerosis (ALS), Parkinson's Disease (PD), Down's Syndrome (DS), glutaric acidaemia, epilepsy, multi-infarct dementia, and encephalitis.

Fourth, the present invention provides the use of the salfaprodil freeze-dried powder injection for use in preparing medicines for the prevention and/or treatment of cerebrovascular and neurological diseases and symptoms.

Preferably, the cerebrovascular and neurological diseases and symptoms are selected from one or more of thromboembolism, ischemic stroke, hemorrhagic stroke, cerebral vasopasm, brain aging, traumatic brain injury, traumatic spinal cord injury, cardiac arrest, arterial hypotension, hypoglycemia, hypoxia, and tissue hypoxia.

Fifth, the present invention provides the use of the salfaprodil freeze-dried powder injection for the prevention and/or treatment of neurodegenerative diseases.

Preferably, the neurodegenerative diseases are selected from one or more of Huntington's Disease (HD), Alzheimer's Disease (AD), Pick's Disease (PD), Korsakov's Syndrome (KS), olivopontocerebellar degeneration, amyotrophic lateral sclerosis (ALS), Parkinson's Disease (PD), Down's Syndrome (DS), glutaric acidemia, epilepsy, multi-infarct dementia, and encephalitis.

Sixth, the present invention provides the use of the salfaprodil freeze-dried powder injection for the prevention and/or treatment of cerebrovascular and neurological diseases.

Preferably, the cerebrovascular and neurological diseases and symptoms are selected from one or more of thromboembolism, ischemic stroke, hemorrhagic stroke, cerebral vasospasm, brain aging, traumatic brain injury, traumatic spinal cord injury, cardiac arrest, arterial hypotension, hypoglycemia, hypoxia, and tissue hypoxia.

Seventh, the present invention provides the method used for the prevention and/or treatment of neurodegenerative diseases, including the administration of a prophylactically and/or therapeutically effective amount of salfaprodil freeze-dried powder injection to individuals in need.

Preferably, neurodegenerative diseases are selected from one or more of Huntington's Disease (HD), Alzheimer's Disease (AD), Pick's Disease (PD), Korsakov's Syndrome (KS), olivopontocerebellar degeneration, amyotrophic lateral sclerosis (ALS), Parkinson's Disease (PD), Down's Syndrome (DS), glutaric acidemia, epilepsy, multi-infarct dementia, and encephalitis.

Eighth, the present invention provides the method used for the prevention and/or treatment of cerebrovascular and neurological diseases and symptoms, including the administration of a prophylactically and/or therapeutically effective amount of salfaprodil freeze-dried powder injection to individuals in need.

Preferably, cerebrovascular and neurological diseases and symptoms are selected from one or more of thromboembolism, ischemic stroke, hemorrhagic stroke, cerebral vasopasm, brain aging, traumatic brain injury, traumatic spinal cord injury, cardiac arrest, arterial hypotension, hypoglycemia, hypoxia, and tissue hypoxia.

Advantages

Compared to the prior art, the present invention has the following advantages:

(1) If freeze-dried powder injection is produced using the preparation method mentioned herein, the solution before freeze-drying will be clear, free from any foreign matter.
(2) The freeze-dried powder injection in the present invention is an off-white powder with fine particles and with a uniform structure.
(3) The freeze-dried powder injection in the present invention has superior re-solubility and shows straw-colored solution with good transparency after reconstitution.
(4) The freeze-dried powder injection in the present invention has a low content of water.
(5) In comparison with the raw materials, the impurity content of the freeze-dried powder injection in the present invention does not increase, and can be effectively controlled.
(6) The parameters of the freeze-dried powder injection of the present invention before and after the 6-month accelerated test can be kept substantially consistent, and the stability is good.

MODE OF CARRYING OUT THE INVENTION

First, the present invention provides a new preparation method of salfaprodil freeze-dried powder injection.

Unless otherwise stated, the term "salfaprodil" used in the present invention refers to any one or multiple forms of potassium 2-hydroxy-5-[2,3,5,6-tetrafluoro-4-(trifluoromethyl)benzylamino]benzoate or a pharmaceutically acceptable salt, hydrate or solvate thereof.

Unless otherwise stated, the term "freeze-dried powder injection" used in the present invention refers to a solid powder formulation prepared by mixing one or more active substances (or ingredients) with one or more excipients in an aseptic environment or dissolving them in a solvent and subjecting them to a certain type of processing (e.g., freeze-drying).

Specifically, the preparation method comprises the following procedures: Adding and dissolving salfaprodil into water for injection; filtering the solution; adjusting pH filtrate with alkaline substance water solution; adding water for injection to achieve constant volume and filling it with inert gas for protection, performing sterile filtration to obtain salfaprodil solution, then freeze-drying the solution to obtain salfaprodil freeze-dried powder injection.

Unless otherwise stated, the term "water for injection" used in the present invention is consistent with the "water for injection" specified in *Chinese Pharmacopoeia* (or *United States Pharmacopoeial European Pharmacopoeia Japanese Pharmacopoeia*).

Unless otherwise stated, the term "dissolving" used in the present invention refers to the operation or process of dissolving a sample in a solvent until the sample is clear or has no visible turbidity or precipitation.

Unless otherwise stated, the term "filtering" used in the present invention refers to the operation or process of separating two phases by making the continuous phase (e.g., liquid in suspension or gas in aerosol of solid particles) of a heterogeneous dispersion (e.g., suspension or aerosol of solid particles) containing solid particles pass through a certain separation medium (e.g., filter paper or filter membrane) under the action of an external force, while the dispersed phase (e.g., solid particles of the heterogeneous dispersion) is captured. If the multi-dispersion is a suspension, the liquid continuous phase passing through the separation medium becomes the "filtrate," and the solid dispersed phase captured by the separation medium becomes the "filter cake." Unless otherwise stated, the definitions of "filtrate" and "filter cake" used in the present invention are as stated above.

In some preferred embodiments, filtering in the preparation method is performed through a filter membrane.

In some preferred embodiments, the pore size of each of the filter membranes for the filtration is 0.2 to 1.0 μm, preferably 0.2 to 0.5 μm, and more preferably 0.45 μm.

In some preferred embodiments, the material of the filter membranes for the filtration was selected from one or more of PES, PTFE, N6/N66, and PVDF.

In some preferred embodiments, the pH of filtrate in the preparation method was adjusted using an alkaline substance water solution.

In some more preferred embodiments, the alkaline substance in the preparation method was selected from potassium hydroxide, potassium carbonate, potassium bicarbonate, sodium hydroxide, sodium carbonate, and sodium bicarbonate; preferably, potassium hydroxide, potassium carbonate, and potassium bicarbonate; and more preferably potassium hydroxide.

In some more preferred embodiments, the molarity of the alkaline substance water solution is 0.1 to 1.0 mol/L and preferably 0.1 to 0.5 mol/L.

In some more preferred embodiments, the alkaline substance water solution was used to adjust the pH of the filtrate to 8.0 to 10.0.

Unless otherwise stated, the term "achieving constant volume" used in the present invention refers to the operation or process of accurately and precisely adding solvent up to the graduation line of the container using an instrument to transfer the liquid (e.g., dropper or pipette) when dissolving or diluting a substance to a certain concentration using a fixed-volume container (e.g., volumetric flask). Simply put, achieving constant volume means adjusting to a fixed volume.

Unless otherwise stated, the term "inert gas" or "chemically inert gas" used in the present invention refers to gaseous substances with no chemical reaction in general test environments. In the periodic table of the elements, they belong to group 0 and include helium (He), neon (Ne), argon (Ar), xenon (Xe), and radon (Rn), commonly referred to as "inert gases." Additionally, nitrogen ($N_2$) and carbon dioxide ($CO_2$), that show no chemical reaction under general conditions, are also included.

In some preferred embodiments, the protection procedure of inert gas in the preparation method involves the provision of an inert atmosphere for the substance that achieved constant volume using inert gas.

In some preferred embodiments, the protection procedure of inert gas in the preparation method involves the provision of an inert atmosphere for the substance that achieved constant volume using argon or nitrogen.

Unless otherwise stated, the term "sterile filtration" or "sterilization by filtration" used in the present invention refers to the operation or process of eliminating bacteria from a sample by means of filtration to achieve asepsis. For sterile filtration, a bacterial filtration apparatus with a fine pore size is commonly used, including a thin-film bacterial filter (also called bacterial filtration membrane or membrane. There are mainly two types of pore sizes: 0.45 μm and 0.22 μm. The latter is more effective in the removal of microorganisms), ceramic bacterial filter, asbestos bacterial filter, and sintered glass bacterial filter.

In some preferred embodiments, sterile filtration in the preparation method is performed using a filter membrane.

In some more preferred embodiments, the pore size of each of the filter membranes for the sterile filtration is 0.20 to 0.22 μm.

In some more preferred embodiments, the material of the filter membrane for the sterile filtration is selected from one or more of PES, PTFE, N6/N66, and PVDF.

In some more preferred embodiments, the sterile filtration is performed within 16 hours, preferably within 12 hours, and more preferably within 8 hours after completely achieving constant volume.

In some preferred embodiments, salfaprodil solution in the preparation method is maintained at an appropriate weight per volume concentration so that the subsequent procedures for freeze-drying can be carried out smoothly.

Unless otherwise stated, the term "weight per volume concentration" (or "mass concentration") used in the present invention refers to the quantity (e.g., 1 g or 1 mg) of the solute contained in a unit volume (e.g., 1 $m^3$ or 1 L) of the solution, and the unit is usually expressed as $g/m^3$ or mg/L, unless otherwise stated, the term "w/v %" used in the present invention refers to the grams of solute per 100 mL of solution, i.e., "g/100 mL."

In some more preferred embodiments, the appropriate weight per volume concentration is 5 to 20 w/v %.

In some preferred embodiments, freeze-drying in the preparation method is performed in a freeze dryer and involves a pre-freezing, temperature recovery, re-cooling, primary drying (primary drying is subdivided into steps a and b according to temperature change), and desorption drying stages.

Unless otherwise stated, the term "freeze-drying" used in the present invention refers to the operation or process of converting (coagulating) a water-containing material (e.g., water-containing medicinal fluid, i.e., salfaprodil solution from the present invention) into ice by freezing it below the freezing point, converting (subliming) the ice into water vapor under a vacuum condition, and removing it. It is permitted to dry the material in a dryer after freezing it in a freezer beforehand or to dry the material after freezing it through rapid vacuum in a dryer. The water vapor generated in the sublimation process is removed by the condensation action of a condenser, and the evaporation heat required in the sublimation process is generally provided by heat radiation or heat conduction.

Unless otherwise stated, the term "freeze dryer" used in the present invention refers to the equipment or device by which freeze-drying is performed, and mainly consists of a sample storage device (including rapid freezing chamber, drying chamber, and optional post-processing chamber), freezing device, vacuum device, heating device, and control device. The principle of operation of the freeze dryer is as follows: transferring the sample to be freeze-dried after pre-processing to the rapid freezing chamber for freezing, then transferring to the drying chamber for sublimation and dehydration, and finally transferring to the post-processing chamber for post-processing. The freezing device provides the cooling capacity necessary for the rapid freezing chamber, and the vacuum device creates a low-pressure condition in the drying chamber. The heating device provides the latent heat for sublimation of the sample, and the control device is used to control commands such as the run/pause/stop of other devices.

In some more preferred embodiments, the plate layer temperature of the freeze dryer is lowered to between −50 to −30° C. and kept at a constant temperature for 1 to 3 hours in the pre-freezing stage during freeze-drying.

In some more preferred embodiments, the plate layer temperature of the freeze dryer is raised to between −5 to 5° C. and kept at a constant temperature for 1 to 3 hours in the temperature recovery stage during freeze-drying.

In some more preferred embodiments, the plate layer temperature of the freeze dryer is lowered to between −50 to −30° C. and kept at a constant temperature for 1 to 3 hours in the re-cooling stage during freeze-drying.

In some more preferred embodiments, the plate layer temperature of the freeze dryer is raised to between −30 to −25° C. and kept at a constant temperature for 10 to 30 hours in the primary drying a stage during freeze-drying. The vacuum degree is 5 to 20 Pa.

In some more preferred embodiments, the plate layer temperature of the freeze dryer is raised to 5 to 20° C. and kept at a constant temperature for 10 to 30 h in the primary drying b step during freeze drying. The vacuum degree is 5 to 20 Pa.

In some more preferred embodiments, the plate layer temperature of the freeze dryer is raised to between 10 to 40° C. and kept at a constant temperature for 10 to 30 hours in the desorption drying stage during freeze-drying. The vacuum degree is 5 to 20 Pa.

Optionally, the preparation method for salfaprodil freeze-dried powder injection in the present invention comprises the steps of filling (or sub-packaging), caulking, capping, and/or packaging. By introducing one or more of the filling (or small packaging), caulking, capping, and/or packaging steps into the preparation method, a freeze-dried powder injection in a certain container (e.g., ampoule or vial) of a certain specification and in a certain packaging format can be ultimately obtained, which is convenient for subsequent storage, transportation, sale, and use.

In addition, the present invention provides salfaprodil freeze-dried powder injection prepared using the preparation method.

In some preferred embodiments, the freeze-dried powder injection contains only one active pharmaceutical ingredient, i.e., salfaprodil.

In addition, the present invention provides the use of the salfaprodil freeze-dried powder injection for the preparation of medicines used for the prevention and/or treatment of neurodegenerative diseases.

Unless otherwise stated, the term "neurodegenerative diseases" used in the present invention refers to complex diseases which develop gradually and may result in impairment and even death, which are characterized by extensive loss of specific neurons and mainly include amyotrophic lateral sclerosis (ALS), Huntington's Disease (HD), Parkinson's Disease (PD), and Alzheimer's Disease (AD).

In some preferred embodiments, the neurodegenerative diseases are selected from one or more of Huntington's Disease (HD), Alzheimer's Disease (AD), Pick's Disease (PD), Korsakov's Syndrome (KS), olivopontocerebellar degeneration, amyotrophic lateral sclerosis (ALS), Parkinson's Disease (PD), Down's Syndrome (DS), glutaric acidemia, epilepsy, multi-infarct dementia, and encephalitis.

In addition, the present invention provides the use of the salfaprodil freeze-dried powder injection for the preparation of medicines for the prevention and/or treatment of cerebrovascular and neurological diseases and symptoms.

In some preferred embodiments, the cerebrovascular and neurological diseases and symptoms are selected from one or more of thromboembolism, ischemic stroke, hemorrhagic stroke, cerebral vasospasm, brain aging, traumatic brain injury, traumatic spinal cord injury, cardiac arrest, arterial hypotension, hypoglycemia, hypoxia, and tissue hypoxia.

The present invention also provides the use of the salfaprodil freeze-dried powder injection as a medicine for the prevention and/or treatment of neurodegenerative diseases.

In some preferred embodiments, the neurodegenerative diseases are selected from one or more of Huntington's Disease (HD), Alzheimer's Disease (AD), Pick's Disease (PD), Korsakov's Syndrome (KS), olivopontocerebellar degeneration, amyotrophic lateral sclerosis (ALS), Parkinson's Disease (PD), Down's Syndrome (DS), glutaric acidemia, epilepsy, multi-infarct dementia, and encephalitis.

The present invention also provides the use of the salfaprodil freeze-dried powder injection as medicine for the prevention and/or treatment of cerebrovascular and neurological diseases and symptoms.

In some preferred embodiments, the cerebrovascular and neurological diseases and symptoms are selected from one or more of thromboembolism, ischemic stroke, hemorrhagic stroke, cerebral vasospasm, brain aging, traumatic brain injury, traumatic spinal cord injury, cardiac arrest, arterial hypotension, hypoglycemia, hypoxia, and tissue hypoxia.

In addition, the present invention provides the method used for the prevention and/or treatment of neurodegenerative diseases, including the administration of a prophylactically and/or therapeutically effective amount of salfaprodil freeze-dried powder injection to individuals in need.

In some preferred embodiments, the neurodegenerative diseases are selected from one or more of Huntington's Disease (HD), Alzheimer's Disease (AD), Pick's Disease (PD), Korsakov's Syndrome (KS), olivopontocerebellar degeneration, amyotrophic lateral sclerosis (ALS), Parkinson's Disease (PD), Down's Syndrome (DS), glutaric acidemia, epilepsy, multi-infarct dementia, and encephalitis.

Finally, the present invention provides the method used for the prevention and/or treatment of cerebrovascular and neurological diseases and symptoms, including the administration of a prophylactically and/or therapeutically effective amount of salfaprodil freeze-dried powder injection to individuals in need.

In some preferred embodiments, the cerebrovascular and neurological diseases and symptoms are selected from one or more of thromboembolism, ischemic stroke, hemorrhagic stroke, cerebral vasospasm, brain aging, traumatic brain injury, traumatic spinal cord injury, cardiac arrest, arterial hypotension, hypoglycemia, hypoxia, and tissue hypoxia.

More specific descriptions of embodiments are presented as follows to explain the present invention in detail. Embodiments are intended to provide a better understanding of the technical methods of the present invention, but technical personnel in the relevant field need to know that the present invention is not limited to these embodiments. Technical personnel in the relevant field can modify the present invention without deviating from the intention and scope of the present invention, and such equivalent modifications also fall within the protected scope of the present invention. Unless otherwise stated, all the medicines, reagents, materials, and instruments used in the following embodiments can be obtained by convention commercial means.

Embodiment 1: Preparation of Salfaprodil

Prepare potassium 2-hydroxy-5-[2,3,5,6-tetrafluoro-4-(trifluoromethyl)benzylamino]benzoate) according to the preparation method in CN1309703C.

Under protection of nitrogen at room temperature, dissolve 5-aminosalicylic acid (102 g) and triethylamine (100 mL) into dry DMF (8,000 mL), and add 2,3,5,6-tetrafluoro-4-(trifluoromethyl) benzyl bromide (123 g) into the solution; stir the reaction mixture for 2 hours at room temperature, and remove the solvent in a vacuum; extract with ethyl acetate/water, and wash the organic layer with water and saline, and dry with anhydrous magnesium sulfate; distill the solvent, elute the residue with ether/n-hexane (1:10) and crystallize to obtain potassium 2-hydroxy-5-[2,3,5,6-tetrafluoro-4-(trifluoromethyl)benzylamino]benzoate (160 g) as a white solid.

Add potassium 2-hydroxy-5-[2,3,5,6-tetrafluoro-4-(trifluoromethyl)benzylamino]benzoate (100 g) into anhydrous ethanol (500 mL), stir while raising the temperature to 50° C. until complete dissolution; cool the solution down to 10° C., adjust the pH of the solution to 6.8 to 7.0 with anhydrous potassium hydroxide ethanolic solution; stir the solution at room temperature for 2 hours, crystallize, filter and dry to obtain salfaprodil (102 g) as an off-white powder, with the purity ≤99.7%. via HPLC test.

Embodiment 2: Preparation of Salfaprodil Freeze-Dried Powder Injection

Dissolve salfaprodil (3,000 g) into water for injection (30 L), purify, and filter through a PES filter membrane with a pore size of 0.45 μm; adjust the pH of the filtrate to 8.2 with 0.1 mol/L of aqueous potassium hydroxide solution, and add water for injection to make 60 L; fill the solution with argon gas for protection and conduct sterile filtering through a PES filter membrane with a pore size of 0.22 μm within 8 hours to obtain a salfaprodil solution.

Put the salfaprodil solution into a vial, and transfer the glass vial a freeze dryer; within 30 minutes, lower the plate layer temperature of the freeze dryer to −50° C. and keep for 1 hour, raise to −5° C. and keep for 1 hour, then lower again to −50° C. and keep for 1 hour; raise to −30° C. and keep under vacuum degree of 5 Pa for 10 hours, and then raise to 10° C. and keep under a vacuum degree of 5 Pa for 10 hours; fill with nitrogen gas at 40 kPa, caulk, cap, and pack.

Embodiment 3: Preparation of Salfaprodil Freeze-Dried Powder Injection

Dissolve salfaprodil (1,500 g) into water for injection (13 L), purify, and filter through a PVDF filter membrane with a pore size of 0.45 μm; adjust the pH of the filtrate to 9.0 with 0.5 mol/L aqueous potassium hydroxide solution, and add water for injection to make 18 L; fill the solution with argon gas for protection and conduct sterile filtering through a PVDF filter membrane with a pore size of 0.22 μm within 4 hours to obtain a salfaprodil solution.

Put the salfaprodil solution into a vial, and transfer the glass vial into a freeze dryer; within 60 minutes, lower the plate layer temperature of the freeze dryer to −40° C. and keep for 2 hours, raise to 0° C. and keep for 2 hours, lower again to −40° C. and keep for 2 hours; then raise to −25° C. and keep under a vacuum degree of 10 Pa for 20 hours, raise to 10° C. and keep under a vacuum degree of 10 Pa for 20 hours, and then raise to 25° C. and keep under a vacuum degree of 10 Pa for 20 hours; fill with nitrogen gas at 65 kPa, caulk, cap, and pack.

Embodiment 4: Preparation of Salfaprodil Freeze-Dried Powder Injection

Dissolve Salfaprodil (3,750 g) into water for injection (15 L), purify, and filter through a PTFE filter membrane with a pore size of 0.45 μm; adjust the pH of the filtrate to 9.8 with 0.8 mol/L aqueous potassium hydroxide solution, and add water for injection to make 19 L; fill the solution with argon gas for protection and conduct sterile filtering through a PTFE filter membrane with a pore size of 0.22 μm within 2 hours to obtain a salfaprodil solution.

Put the salfaprodil solution into a vial, and transfer the glass vial into a freeze dryer; within 90 minutes, lower the plate layer temperature of the freeze dryer to −30° C. and keep for 3 hours, raise to 5° C. and keep for 3 hours; lower again to −30° C. and keep for 3 hours; raise to −20° C. and keep under a vacuum degree of 20 Pa for 30 hours; raise to 5° C. and keep under a vacuum degree of 20 Pa for 30 hours, and then raise to 40° C. and keep under a vacuum degree of 20 Pa for 30 hours; fill with nitrogen gas at 90 kPa, caulk, cap, and pack.

In embodiments 2 through 4, the outcomes of parameters for salfaprodil freeze-dried powder injection including appearance (Common Provisions, Part 4, 2015 Edition of *Chinese Pharmacopoeia*), reconstitution time, solution transparency, and solution color (Appendix IX B, 2015 Edition of *Chinese Pharmacopoeia*), water content (Common Provision 0832, Part 4, 2015 Edition of *Chinese Pharmacopoeia*), related substances (Common Provision 0512, Part 4, 2015 Edition of *Chinese Pharmacopoeia*), and stability are presented in Table 1.

TABLE 1

Outcomes Of Parameters For Salfaprodil Freeze-Dried Powder Injection

| Parameter | | Substance | Embodiment 2 | Embodiment 3 | Embodiment 4 | Embodiment 2 (6-month accelerated stability) |
|---|---|---|---|---|---|---|
| Appearance | | Off-white powder | Off-white powder | Off-white powder | Off-white powder | Off-white powder |
| Reconstitution time | | / | 5 s | 7 s | 5 s | 5 s |
| Solution transparency and color | | / | Straw-colored, clear | Straw-colored, clear | Straw-colored, clear | Straw-colored, clear |
| Water content | | 0.2% | 0.1% | 0.1% | 0.2% | 0.1% |
| Related substances | 5-aminosalicylic acid | 0.05% | 0.05% | 0.05% | 0.05% | 0.05% |
| | Other individual impurities | 0.02% | 0.02% | 0.02% | 0.02% | 0.02% |
| | Total impurities | 0.1% | 0.1% | 0.1% | 0.1% | 0.1% |

Through the embodiments 2~4, the invention prepared 3 batches of salfaprodil freeze-dried powder, and all of the products of each batch showed the following effects.

(1) When freeze-dried powder injection is produced using the preparation method mentioned herein, the solution before freeze-drying is visually clear and shows no foreign matter.

(2) The freeze-dried powder injection in the present invention is an off-white powder with fine particles and a uniform structure.

(3) The freeze-dried powder injection in the present invention has effective re-solubility (reconstitution time: within 10 s). The post-reconstitution solution is straw-colored and has good transparency.

(4) The freeze-dried powder injection in the present invention has a low content of water (≤0.2%).

(5) In comparison with the raw materials, the impurity content of the freeze-dried powder injection in the present invention does not increase and can be effectively controlled.

(6) The parameters of the freeze-dried powder injection of the present invention before and after the 6-month accelerated test can be kept substantially consistent, and the stability is good.

What is claimed is:

1. A method for preparing salfaprodil freeze-dried powder injection, the method comprising:

adding and dissolving salfaprodil into water to generate a solution for injection;

filtering the solution;

adjusting pH filtrate with an alkaline substance water solution to the value of from 8.0 to 10.0;

adding water for injection to achieve constant volume and filling it with inert gas for protection;

performing sterile filtration to obtain a salfaprodil solution; and freeze-drying the salfaprodil solution to obtain a salfaprodil freeze-dried powder injection, wherein the freeze-drying is conducted in a freeze dryer, and the method comprises pre-freezing, a temperature recovery, re-cooling, primary drying a, primary drying b, and desorption drying;

wherein the pre-freezing comprises lowering the plate layer temperature of the freeze dryer to a temperature of −50° C. to −30° C. and keeping this temperature for 1 hour to 3 hours;

wherein the temperature recovery comprises raising the plate layer temperature of the freeze dryer to a temperature of −5° C. to 5° C. and keeping this temperature for 1 hour to 3 hours;

wherein the re-cooling comprises lowering the plate layer temperature of the freeze dryer to a temperature of −50° C. to −30° C. and keeping this temperature for 1 hour to 3 hours;

wherein the primary drying a comprises raising the plate layer temperature of the freeze dryer to a temperature of −30° C. to −25° C. and keeping this temperature for 10 hours to 30 hours under a vacuum degree of 5 Pa to 20 Pa;

wherein the primary drying b comprises raising the plate layer temperature of the freeze dryer to a temperature of 5° C. to 20° C. and keeping this temperature for 10 hours to 30 hours under a vacuum degree of 5 Pa to 20 Pa; and wherein the desorption drying comprises raising the plate layer temperature of the freeze dryer to a temperature of 10° C. to 40° C. and keeping this temperature for 10 hours to 30 hours under a vacuum degree of 5 Pa to 20 Pa.

2. The method according to claim 1, wherein:

the pore size of each of the filter membranes used for filtration and sterile filtration in the preparation method is 0.2 μm to 1.0 μm.

3. The method according to claim 1, wherein:

alkaline substance of the alkaline substance water solution is selected from potassium hydroxide, potassium carbonate, potassium bicarbonate, sodium hydroxide, sodium carbonate, or sodium bicarbonate.

4. The method according to claim 1, wherein: sterile filtration is performed within 16 hours after achieving the constant volume.

5. The method according to claim 1, wherein: the weight per volume concentration of the salfaprodil solution is 5 w/v % to 20 w/v %.

6. A salfaprodil freeze-dried powder injection prepared by the method of claim 1.

7. A method for prevention and/or treatment of neurodegenerative disease, the method comprising:

administering a prophylactically and/or therapeutically effective amount of a salfaprodil freeze-dried powder injection of claim 6 to one or more individuals in need thereof, wherein the neurodegenerative disease is one or more selected from the group consisting of Huntington's disease, Alzheimer's disease, Pick's disease, Korsakov's syndrome, olivopontocerebellar degeneration, amyotrophic lateral sclerosis, Parkinson's disease, Down's syndrome, glutaric acidemia, epilepsy, multi-infarct dementia, and encephalitis.

8. A method for prevention and/or treatment of cerebrovascular and neurological diseases and symptoms, the method comprising:

Administering a prophylactically and/or therapeutically effective amount of a salfaprodil freeze-dried powder injection of claim 6 to one or more individuals in need thereof, wherein the cerebrovascular and neurological diseases and symptoms is one or more selected from the group consisting of thromboembolism, ischemic stroke, hemorrhagic stroke, cerebral vasospasm, brain aging, traumatic brain injury, traumatic spinal cord injury, cardiac arrest, arterial hypotension, hypoglycemia, hypoxia, and tissue hypoxia.

* * * * *